(12) United States Patent
Hoyt

(10) Patent No.: US 10,032,064 B2
(45) Date of Patent: Jul. 24, 2018

(54) VISUALIZATION AND MEASUREMENT OF CELL COMPARTMENTS

(71) Applicant: Cambridge Research & Instrumentation, Inc., Hopkinton, MA (US)

(72) Inventor: Clifford C. Hoyt, Wellesley, MA (US)

(73) Assignee: Cambridge Research & Instrumentation, Inc., Hopkinton, MA (US)

(*) Notice: Subject to any disclaimer, the term of this patent is extended or adjusted under 35 U.S.C. 154(b) by 488 days.

(21) Appl. No.: 13/972,119

(22) Filed: Aug. 21, 2013

(65) Prior Publication Data
US 2014/0056505 A1  Feb. 27, 2014

Related U.S. Application Data

(60) Provisional application No. 61/691,752, filed on Aug. 21, 2012.

(51) Int. Cl.
G06K 9/00 (2006.01)
G01N 1/30 (2006.01)
(Continued)

(52) U.S. Cl.
CPC .......... *G06K 9/00127* (2013.01); *G01N 1/30* (2013.01); *G01N 21/6428* (2013.01); *G01N 21/6456* (2013.01); *G02B 21/365* (2013.01); *G06T 7/90* (2017.01); *G01N 21/6458* (2013.01); *G01N 2021/6417* (2013.01); *G01N 2021/6441* (2013.01); *G01N 2021/6471* (2013.01); *G06T 2207/10016* (2013.01); *G06T 2207/10024* (2013.01); *G06T 2207/10056* (2013.01);
(Continued)

(58) Field of Classification Search
CPC .......... G06T 7/408; G06T 2207/10024; G06T 2207/10056; G06K 9/00; G02B 21/365
See application file for complete search history.

(56) References Cited

U.S. PATENT DOCUMENTS 6,365,362 B1 * 4/2002 Terstappen et al. ......... 435/7.23
7,282,350 B2 * 10/2007 Rao et al. .................... 435/40.5
(Continued)

OTHER PUBLICATIONS

Chris M. Van Der Loos, Chromogens in Multiple Immunohistochemical Staining Used for Visual Assesment and Spectral Imaging: The Colorful Future, Mar. 2010, Academic Medical Center, Department of Pathology, The Journal of Histotechnology, vol. 33, No. 1, pp. 31-40.*
(Continued)

Primary Examiner — Gregory M Desire
(74) Attorney, Agent, or Firm — Fish & Richardson P.C.

(57) ABSTRACT

The disclosure features methods and systems that include a detector configured to obtain multiple images of a sample stained with first and second stains, where the first and second stains have similar spectral absorption and emission profiles, and an electronic processor configured to decompose the multiple images into an unmixed image set, where the unmixed image set includes a first unmixed image corresponding to the first stain and a second unmixed image corresponding to the second stain, and identify nuclear regions in the sample based on the first unmixed image and identify cytoplasm regions in the sample based on the second unmixed image.

34 Claims, 6 Drawing Sheets

(51) Int. Cl.
*G01N 21/64* (2006.01)
*G02B 21/36* (2006.01)
*G06T 7/90* (2017.01)

(52) U.S. Cl.
CPC ............ *G06T 2207/10064* (2013.01); *G06T 2207/10152* (2013.01); *G06T 2207/30024* (2013.01)

(56) References Cited

U.S. PATENT DOCUMENTS

| | | | | |
|---|---|---|---|---|
| 7,689,023 | B2* | 3/2010 | Rabinovich | G06K 9/00127 382/128 |
| 8,093,012 | B2* | 1/2012 | Hamann et al. | 435/7.23 |
| 2005/0009032 | A1* | 1/2005 | Coleman | G06K 9/0014 435/6.16 |
| 2008/0272312 | A1* | 11/2008 | Tuschel | 250/459.1 |
| 2009/0226059 | A1 | 9/2009 | Levenson et al. | |
| 2009/0324051 | A1 | 12/2009 | Hoyt et al. | |
| 2012/0010528 | A1 | 1/2012 | Donovan et al. | |
| 2012/0121505 | A1* | 5/2012 | Gill et al. | 424/1.49 |
| 2012/0134927 | A1 | 5/2012 | Jahn-Hofmann et al. | |
| 2012/0157476 | A1 | 6/2012 | Hebeisen et al. | |
| 2017/0154420 | A1* | 6/2017 | Barnes | G06T 7/0012 |
| 2017/0169567 | A1* | 6/2017 | Chefd'hotel | G06K 9/00127 |
| 2017/0206655 | A1* | 7/2017 | Chen | G06T 7/0012 |
| 2017/0270346 | A1* | 9/2017 | Ascierto | G06K 9/00147 |

OTHER PUBLICATIONS

International Preliminary Report on Patentability and Written Opinion of the International Searching Authority for International Application No. PCT/US2013/055969 dated Mar. 5, 2015 (12 pages).
International Search Report and the Written Opinion of the International Searching Authority for International Application No. PCT/US2013/055969 dated Dec. 6, 2013 (17 pages).
"HCS CellMask™ stains" *Molecular Probes. E Invitrogen*, dated Apr. 7, 2009 (5 pages) Retrieved from the Internet: URL:http://tools.lifetechnologies.com/content/sfs/manuals/mp32712.pdf [retrieved on Nov. 27, 2013].
Office Action for Chinese Application No. 2013800534765, dated Jul. 27, 2016 (20 pages).
Office Action from the Chinese Patent Office for Chinese Application No. 2013800534765 dated Jun. 7, 2017.
Chinese Office Action for Chinese Application No. 2013800534765 dated Mar. 6, 2018.

* cited by examiner

VISUALIZATION AND MEASUREMENT OF CELL COMPARTMENTS

CROSS-REFERENCE TO RELATED APPLICATIONS

This application claims priority to U.S. Provisional Patent Application No. 61/691,752, filed on Aug. 21, 2012, the entire contents of which are incorporated herein by reference.

TECHNICAL FIELD

This disclosure relates to imaging of biological samples, including cells and tissue samples.

BACKGROUND

Stains and fluorescent agents are widely used to visualize structures in cells and tissues. For example, in pathology, it is common to use a hematoxylin and eosin stain preparation (H&E) to visualize structures in cells and tissue. Information obtained from cells stained in this manner can be used to identify cell types, or tissue structures, or to diagnose disease. Other preparations, such as papanicolaou stain, can also be useful for the same broad purpose. These stains are used in brightfield microscopy, where a stained sample is viewed by observing light transmitted through the sample. Absorption or scattering by the stain produces color or contrast in the image of the sample.

DAPI (4',6-diamidino-2-phenylindole) is a fluorescent counterstain that binds to DNA molecules in nuclei of cells and tissue. It is widely used in fluorescence microscopy to determine the location or presence of nuclei in a sample. In this technique, the sample is excited with light of one wavelength, typically in the 350-370 nm ultraviolet range, and the sample emits light in the violet region of the spectrum. The Hoechst 33258 stain is used for similar purposes, and has excitation and emission properties that are similar to those of DAPI.

Immunofluorescent (IF) probes are useful to image the presence, location, and amount of proteins in cells and tissue. The use of such probes enables highly specific measurements for a variety of research and clinical tasks. Techniques have been developed for applying multiple immunofluorescent probes to a single sample. Optical cross-talk and other factors such as antibody interaction and non-specific binding can limit the number of probes that can be used, and can degrade the accuracy or reduce the useful protein expression range.

SUMMARY

The systems and methods disclosed herein use counterstains with similar absorption and emission profiles as markers for different sub-cellular regions within a sample. Because these counterstains have similar emission profiles, in general they cannot be distinguished visually from one another in a fluorescence image of a sample. Spectral unmixing techniques can be used to separate the contributions of each of these counterstains in multispectral images. Unmixed images can be used to identify sub-cellular regions within the sample, such as nuclei and cytoplasm regions in one or more cells within the sample. One or more IF probes can be applied to the samples to locate and quantitate specific molecular entities such as proteins within the different regions of the sample. In some embodiments, a view is produced from the unmixed images of the counterstains that simulates how the sample would have appeared, if it were prepared with H&E stains, and viewed in a brightfield microscope. This provides valuable context information about the sample that is otherwise missing in fluorescence images.

In general, in a first aspect, the disclosure features systems that include a detector configured to obtain multiple images of a sample stained with first and second stains, where the first and second stains have similar spectral absorption and emission profiles, and an electronic processor configured to: decompose the multiple images into an unmixed image set, where the unmixed image set includes a first unmixed image corresponding to the first stain and a second unmixed image corresponding to the second stain; and identify nuclear regions in the sample based on the first unmixed image and identify cytoplasm regions in the sample based on the second unmixed image.

Embodiments of the systems can include any one or more of the following features.

The electronic processor can be configured to generate an image of the sample, where the nuclear and cytoplasm regions in the image are colored in the same manner as if the sample was stained with hematoxylin and eosin.

The sample can include one or more immunofluorescent probes, and the unmixed image set can include unmixed images that each correspond to contributions from only one of the immunofluorescent probes. The electronic processor can be configured to determine an amount of at least some of the immunofluorescent probes in the nuclear and cytoplasm regions in the sample. The sample can include at least three immunofluorescent probes (e.g., at least five immunofluorescent probes).

The multiple images can include fluorescence images. The second stain can be CellMask Blue. The first stain can be DAPI. The first stain can be Hoechst 33258. The multiple images can define an image cube. Each of the multiple images can correspond to a fluorescence image of the sample for a different corresponding range of fluorescence wavelengths.

The systems can include a multi-spectral imaging system coupled to the detector, where the multi-spectral imaging system is configured to illuminate the sample to obtain the multiple images.

Embodiments of the systems can also include any of the other features disclosed herein, in any combination, as appropriate.

In another aspect, the disclosure features methods that include applying at least two stains to a sample, where the at least two stains have similar spectral absorption and emission profiles, and identifying nuclear and cytoplasm regions in the sample based on absorption or emission of light by the at least two stains.

Embodiments of the methods can include any one or more of the following features.

The methods can include obtaining multiple images of the sample, decomposing the multiple images into an unmixed image set, where the unmixed image set includes a first unmixed image corresponding to a first one of the stains and a second unmixed image corresponding to a second one of the stains, and identifying the nuclear regions based on the first unmixed image and identifying the cytoplasm regions based on the second unmixed image.

The methods can include generating an image of the sample, where the nuclear and cytoplasm regions in the image are colored in the same manner as if the sample was stained with hematoxylin and eosin.

The sample can include one or more immunofluorescent probes, and the unmixed image set can include unmixed images that each correspond to contributions from only one of the immunofluorescent probes. The methods can include determining an amount of at least some of the immunofluorescent probes in the nuclear and cytoplasm regions in the sample. The sample can include at least three immunofluorescent probes (e.g., at least five immunofluorescent probes). The multiple images can include fluorescence images. The at least two stains can include CellMask Blue and DAPI. The at least two stains can include CellMask Blue and Hoechst 33258. The multiple images can define an image cube. Each of the multiple images can correspond to a fluorescence image of the sample for a different corresponding range of fluorescence wavelengths.

Embodiments of the methods can also include any of the other features or steps disclosed herein, in any combination, as appropriate.

In a further aspect, the disclosure features systems that include a detector configured to obtain multiple images of a sample stained with first and second stains, where the first stain includes DAPI or Hoeschst 33258 and the second stain includes CellMask Blue, and an electronic processor configured to: decompose the multiple images into an unmixed image set, where the unmixed image set includes a first unmixed image corresponding to the first stain and a second unmixed image corresponding to the second stain; and identify nuclear regions in the sample based on the first unmixed image and identify cytoplasm regions in the sample based on the second unmixed image.

Embodiments of the systems can include any one or more of the following features.

The electronic processor can be configured to generate an image of the sample, where the nuclear and cytoplasm regions in the image are colored in the same manner as if the sample was stained with hematoxylin and eosin.

The sample can include one or more immunofluorescent probes, where the unmixed image set includes unmixed images that each correspond to contributions from only one of the immunofluorescent probes. The electronic processor can be configured to determine an amount of at least some of the immunofluorescent probes in the nuclear and cytoplasm regions in the sample.

Embodiments of the systems can also include any of the other features disclosed herein, in any combination, as appropriate.

In another aspect, the disclosure features methods that include applying at least two stains to a sample, where the first stain includes DAPI or Hoeschst 33258 and the second stain includes CellMask Blue, and identifying nuclear and cytoplasm regions in the sample based on absorption or emission of light by the at least two stains.

Embodiments of the methods can include any one or more of the following features.

The methods can include obtaining multiple images of the sample, decomposing the multiple images into an unmixed image set, where the unmixed image set includes a first unmixed image corresponding to a first one of the stains and a second unmixed image corresponding to a second one of the stains, and identifying the nuclear regions based on the first unmixed image and identifying the cytoplasm regions based on the second unmixed image.

The methods can include generating an image of the sample, where the nuclear and cytoplasm regions in the image are colored in the same manner as if the sample was stained with hematoxylin and eosin. The sample can include one or more immunofluorescent probes, and the unmixed image set can include unmixed images that each correspond to contributions from only one of the immunofluorescent probes. The methods can include determining an amount of at least some of the immunofluorescent probes in the nuclear and cytoplasm regions in the sample.

Embodiments of the methods can also include any of the other features or steps disclosed herein, in any combination, as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
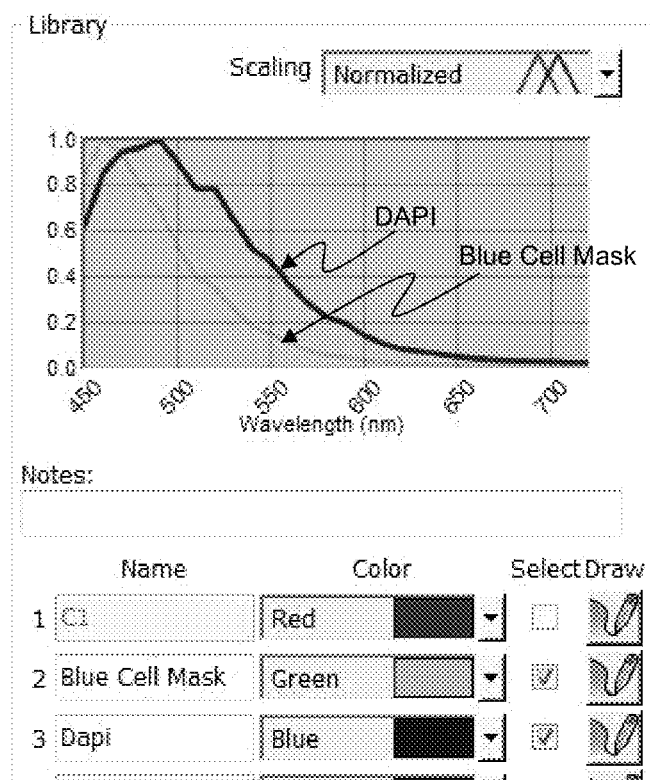
FIG. 1 is a graph showing emission spectra for CellMask Blue and DAPI stains, measured from samples prepared with these stains.

Conventional approaches to identifying different subcellular regions within tissues and cells (and in particular, to identifying regions corresponding to nuclei and regions corresponding to cytoplasm) involve applying multiple counterstains to a sample, where one of the applied counterstains is used to identify the nuclear regions and the other is used to identify the cytoplasm. These stains are typically selected such that their absorption or emission profiles are well separated spectrally. By changing the wavelength of light used to illuminate the sample, each stain can each be selectively interrogated, and regions of the sample that correspond to nuclei and cytoplasm can be distinguished from one another. In an image the sample, each pixel can be assigned to either nuclear regions or cytoplasm regions.

Alternatively, a multi-band excitation filter may be used, and both counterstains may be excited simultaneously; provided the counterstains have well-separated emission profiles, typically corresponding to different colors, a color camera or human observer can distinguish nuclear regions from cytoplasm regions based on differences in color in the resulting emission.

However, the use of two counterstains with markedly different absorption profiles can render a significant amount of the visual portion of the electromagnetic spectrum unavailable for other imaging purposes. Specifically, the number and type of IF probes, which can be used to identify specific types of proteins and other entities, is reduced because the parts of the spectrum used by the counterstains are unavailable for use by IF probes.

In contras to conventional staining protocols for identifying the nuclear and cytoplasm regions, the systems and methods disclosed herein use counterstains that have similar spectral absorption profiles to identify the nuclear and cytoplasm regions. In this way, most of the visual portion of the spectrum remains available for use with IF probes. Relative to conventional staining protocols, a larger number of IF probes can be used with a single sample, providing a multiplex advantage in which more information can be acquired from the sample. In addition, by acquiring information from a single sample, variations in measurement results that might otherwise result from sample-to-sample differences can be eliminated. For example, one learns the relative values, and ratios, of multiple proteins within an individual cell, which can be highly informational about cell signaling behavior.

Moreover, in part because of their similar spectral absorption profiles, the counterstains used in this invention to identify nuclear and cytoplasm regions within the sample also have similar spectral emission profiles. As a result, the counterstains are typically indistinguishable to the unaided human eye in an image of a sample to which both stains have been applied. However, spectral unmixing methods, described in further detail below, can be used to separate contributions to spectral images from each of these stains, so that different sample regions can be identified. One example of a pair of counterstains which satisfies these criteria is DAPI (which is used to identify nuclear regions) and CellMask Blue (which is used to identify cytoplasm). Another example of a pair of counterstains which satisfies these criteria is Hoechst 33258 (which is used to identify nuclear regions) and CellMask Blue.

By appropriate choice of the counterstains used to identify the sample regions (e.g., nuclear regions and cytoplasm regions), spectral cross-talk between the counterstains and IF probes can be reduced or eliminated. This enhances the reliability of quantitative information extracted from measurements of fluorescence from the IF probes. For example, in some embodiments, samples are stained with DAN to identify nuclear regions and with CellMask Blue to identify cytoplasm. Neither of these counterstains strongly absorbs light in the visual portion of the electromagnetic spectrum. That means that fluorescence from many IF probes is not significantly absorbed by the counterstains. And, the counterstains are not excited by the visible light used to excite common IF probes. As a result, more such IF probes can be applied to the same samples to target particular molecular structures without interference or spectral-crosstalk from the counterstains. This increases the number of proteins or other compounds of interest that can be measured. Similar advantages can also be realized when other counterstains having suitable spectral properties are used to identify the nuclear and cytoplasm regions.

Another advantage is realized in embodiments when the stains used to identify sample regions are not themselves antibody-based. For example, CellMask Blue is a simple counterstain that is not antibody-based, and it does not interfere with other antibodies used in IF probe labeling. The same is true of DAPI and the Hoechst stains. Thus from the perspective of antibody interactions, as well as optical interference, they do not limit the number of IF probes that can be applied to a sample, reduce the accuracy of quantitative results obtained from IF probes, or reduce the useful protein expression range that can be detected.

Yet another advantage of the present invention is that, because the cytoplasm information is derived with little additional complexity, and does not reduce the number of IF probes that can be used, cytoplasm information can be obtained in experiments where it would otherwise not have been available at all, or would have come at the expense of valuable IF information. Overall, the effect in many cases is to make it practical to obtain cytoplasm information, which otherwise would have been absent.

The systems and methods disclosed herein also enable the synthesis and display of images based on acquired measurement data. For example, in some embodiments, the systems and methods provide for treating a biological sample with fluorescent agents (e.g., IF probes), imaging the sample in a multispectral imaging system, and generating a digitally synthesized image that is visually similar in appearance to the appearance that the sample would have had if it had been prepared with H&E and viewed in a brightfield microscope. Such a view is termed a digital H&E view.

By obtaining information about regions (e.g., nuclear and cytoplasm regions) within the sample, and about the location of various IF probes within the sample, the immunofluorescent signal from each of the IF probes can be quantitated and associated with the regions within the sample. For example, the amount of a particular immunofluorescent signal associated with nuclear regions and with cytoplasm regions of a sample can be determined. Further, for each of the different types of regions (e.g., nuclear and cytoplasm) in one or more cells, multiple immunofluorescent signals can be quantitated. Digital images can display the locations of nuclear regions, cytoplasm regions, or both. Such images can also display the locations of one or more IF probes within these regions.

As used herein, "stain" refers to the compound or structure (e.g., a dye) that provides the spectral signature for the stained component of interest. For example, the spectral signature corresponds to the spectral distribution of absorption or emission from the stain. The term "counterstain" refers particularly to stains that do not provide high degree of molecular specificity, but instead, generally bind to certain physiological structures when applied to a sample. For example, DAPI is a well-known fluorescent dye that can be applied to a biological sample to provide spatial context and landmarks. Specifically, DAPI preferentially binds to nuclei and thereby provides contrast between nuclear and non-nuclear components of the cell. But it does not have the high degree of molecular specificity associated with IF probes. Other examples of counterstains that can be used with the methods and systems disclosed herein include CellMask Blue, Hoechst 33258 and Hoechst 33342.

IF probes may incorporate fluorescent moieties such as fluorescein, rhodamine, the Alexa series of fluors (available from InVitrogen, Carlsbad, Calif.), tetramethyl rhodamine isothiocyanate (TRITC), the Cy series of fluors (available from GE Healthcare Biosciences, Pittsburgh, Pa.), or other fluors, according to factors such as cost or individual preferences, the capabilities of the imaging equipment, available materials, and other factors that may arise, so long as the excitation or emission properties are distinct from those of the counterstains. Alternatively, the IF probes may use quantum dots rather than fluorescent molecules to generate emitted light.

Multispectral Imaging Systems

Figure 6:
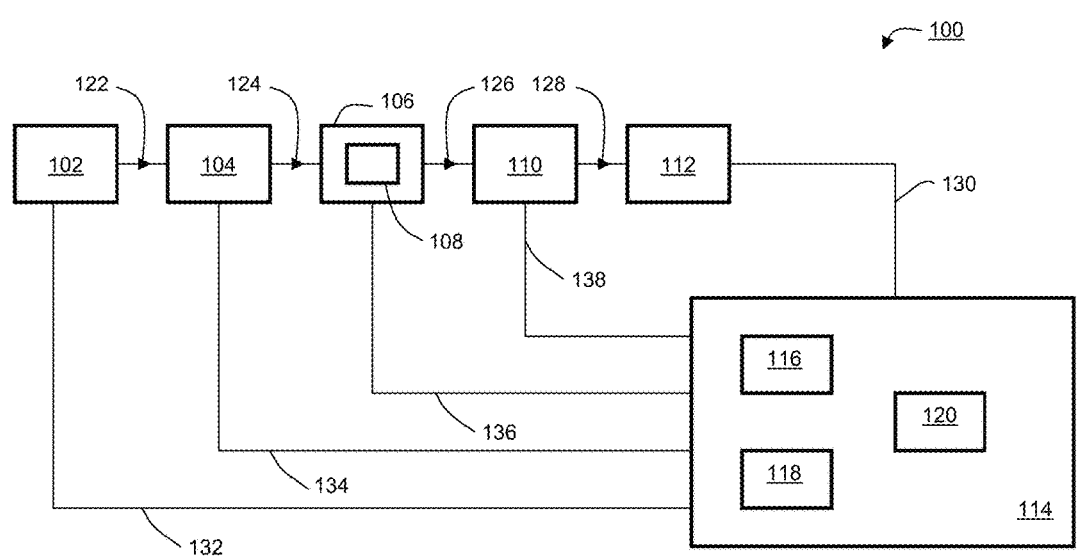
FIG. 6 is a schematic diagram of a system for acquiring multiple spectrally resolved images of a sample.

After a sample has been stained using counterstains with similar absorption and emission profiles that are separately used to identify different sample regions (e.g., nuclear and cytoplasm regions), and optionally one or more IF probes have been applied to the sample, the sample is imaged in a multispectral imaging system to obtain one or more images of the sample. FIG. 6 is a schematic diagram showing a system 100 for acquiring multiple spectrally resolved images of a sample. A light source 102 provides light 122 to light conditioning optics 104. Light 122 can be incoherent light, such as light generated from a filament source for example, or light 122 can be coherent light, such as light generated by a laser. Light 122 can be either continuous-wave (CW) or time-gated (i.e., pulsed) light. Further, light 122 can be provided in a selected portion of the electromagnetic spectrum. For example, light 122 can have a central wavelength and/or a distribution of wavelengths that falls within the ultraviolet, visible, infrared, or other regions of the spectrum.

Light conditioning optics 104 can be configured to transform light 122 in a number of ways. For example, light conditioning optics 104 can spectrally filter light 122 to provide output light in a selected wavelength region of the spectrum. Alternatively, or in addition, light conditioning optics can adjust the spatial distribution of light 122 and the temporal properties of light 122. Incident light 124 is generated from light 122 by the action of the elements of light conditioning optics 104.

Incident light 124 is directed to be incident on sample 108 mounted on illumination stage 106. Stage 106 can provide means to secure sample 108, such as mounting clips or other fastening devices. Alternatively, stage 106 can include a movable track or belt on which a plurality of samples 108 are affixed. A driver mechanism can be configured to move the track in order to successively translate the plurality of samples, one at a time, through an illumination region on stage 106, whereon incident light 124 impinges. Sample 108 may further be held in a carrier or cassette to facilitate handling. Stage 106 can further include translation axes and mechanisms for translating sample 108 relative to a fixed position of illumination stage 106. The translation mechanisms can be manually operated (e.g., threaded rods) or can be automatically movable via electrical actuation (e.g., motorized drivers, piezoelectric actuators).

In response to incident light 124, emitted light 126 emerges from sample 108. Typically, incident light 124 is absorbed by sample 108, and emitted light 126 corresponds to fluorescence emission from sample 108 in response to incident light 124.

In some embodiments, sample 108 is a pathology sample from a human or an animal. It may be a tissue section or fine-needle aspirate. In certain embodiments, the sample is a collection of cells obtained by swabbing or scraping the lungs, cervix, gastro-intestinal tract, or another organ. In some embodiments, the sample can include cells obtained from blood, sputum, or other biological fluids. In particular, in some embodiments, the sample can include blood samples being assayed for circulating tumor cells or other rare cells. In some embodiments, sample 108 can include individual bacteria or other microorganisms, or cells from a cell culture. The cells or tissue in sample 108 may be live, fixed, or more generally in any state as desired.

Light collecting optics 110 are positioned to received emitted light 126 from sample 108. Light collecting optics 110 can be configured to collimate emitted light 126 when light 126 is divergent, for example. Light collecting optics 110 can also be configured to spectrally filter emitted light 126. Filtering operations can be useful, for example, in order to isolate a portion of emitted light 126 arising via one of the mechanisms discussed above from light arising via other processes. Further, light collecting optics 110 can be configured to modify the spatial and/or temporal properties of emitted light 126 for particular purposes in embodiments. Light collecting optics 110 transform emitted light 126 into output light 128 which is incident on detector 112.

Detector 112 includes one or more elements such as CCD sensors or scientific CMOS imaging sensors configured to detect output light 128. In some embodiments, detector 112 can be configured to measure the spatial and/or temporal and/or spectral properties of light 128. Detector 112 generates an electrical signal that corresponds to output light 128, and is communicated via electrical communication line 130 to electronic control system 114.

Electronic control system 114 includes a processor 116, a display device 118, and a user interface 120. In addition to receiving signals corresponding to output light 128 detected by detector 112, control system 114 sends electrical signals to detector 112 to adjust various properties of detector 112. For example, if detector 112 includes a CCD sensor, control system 114 can send electrical signals to detector 112 to control the exposure time, active area, gain settings, and other properties of the CCD sensor.

Electronic control system 114 also communicates with light source 102, light conditioning optics 104, illumination stage 106, and light collecting optics 110 via electrical communication lines 132, 134, 136, and 138, respectively. Control system 114 provides electrical signals to each of these elements of system 100 to adjust various properties of the elements. For example, electrical signals provided to light source 102 can be used to adjust the intensity, wavelength, repetition rate, or other properties of light 122. Signals provided to light conditioning optics 104 and light collecting optics 110 can include signals for configuring properties of devices that adjust the spatial properties of light (e.g., spatial light modulators) and for configuring spectral filtering devices, for example. Signals provided to illumination stage 106 can provide for positioning of sample 108 relative to stage 106 and/or for moving samples into position for illumination on stage 106, for example.

Control system 114 includes a user interface 120 for displaying system properties and parameters, and for displaying captured images of sample 108. User interface 120 is provided in order to facilitate operator interaction with, and control over, system 100. Processor 116 includes a storage device for storing image data captured using detector 112, and also includes computer software that embodies instructions to processor 116 that cause processor 116 to carry out control functions, such as those discussed above for example.

In general, system 100 is configured to acquire multiple spectral images of sample 108. The multiple spectral images may correspond to illumination of sample 108 at a variety of selected wavelengths of light, and detecting an intensity of light emitted by sample 108. Some of the multiple spectral images may correspond to illumination of sample 108 with light having similar spectral properties, and collecting multiple images of sample 108, each image corresponding to a different wavelength of emitted light 126. Spectral filtering elements in light conditioning optics 104 and light collecting optics 110 are generally used to obtain the spectrally resolved data.

In some embodiments, images of sample 108 can be collected in sequence, with adjustments to the configuration of optical components (e.g., optical filters) between successive captured images. In other embodiments, multiple images can be captured simultaneously using detection systems configured to detect multiple sample views. For example, detection systems can be configured to project different views of the sample corresponding to different emission wavelengths onto a detector such as a CCD camera, or onto multiple such detectors, and the multiple views can be captured simultaneously.

In some embodiments, light conditioning optics 104 include an adjustable spectral filter element such as a filter wheel or a liquid crystal spectral filter. The filter element can be configured to provide for illumination of sample 108 using different light wavelength bands. Light source 102 can provide light 122 having a broad distribution of spectral wavelength components. A selected region of this broad wavelength distribution is allowed to pass as incident light 124 by the filter element in light conditioning optics 104, and directed to be incident on sample 108. An image of light 126 emitted by sample 108 is recorded by detector 112. Subsequently, the wavelength of the filter pass-band in light conditioning optics 104 is changed to provide incident light 124 having a different wavelength, and an image of light 126 transmitted through sample 108 (and corresponding to the new wavelength of incident light 124) is recorded. A similar set of spectrally-resolved images can also be recorded by employing a light source 102 having multiple source elements generating light of different wavelengths, and alternately turning the different source elements on and off to provide incident light 124 having different wavelengths.

Emitted light 126 from sample 108 typically includes light corresponding to fluorescence emission from fluorescent chemical structures within sample 108. In some embodiments, emitted light 126 can also include one or more additional contributions, e.g., portions of incident light 124 that are reflected by, scattered by, or transmitted through sample 108. Where emitted light 126 includes one or more additional contributions, the spectral filtering elements in light conditioning optics 110 can be used to separate these contributions from the fluorescence emission.

In general, both light conditioning optics 104 and light collecting optics 110 may include configurable spectral filter elements. Therefore, spectral resolution can be provided either on the excitation side of sample 108 (e.g., via light conditioning optics 104) or on the emission side of sample 108 (e.g., via light collecting optics 110), or both. In any case, the result of collecting multiple, spectrally resolved images of sample 108 is an "image stack" where each image in the stack is a two-dimensional image of the sample corresponding to a particular combination of excitation and emission wavelengths. Conceptually, the set of images can be visualized as forming a three-dimensional matrix, where two of the matrix dimensions are the spatial length and width of each of the images, and the third matrix dimension is the spectral configuration, i.e. the combination of emission and excitation wavelengths to which the image corresponds. For this reason, the set of spectrally resolved images can be referred to as a "spectral cube" of images. As used herein, a "pixel" in such a set of images (or image stack or spectral cube), refers to a common spatial location for each of the images. Accordingly, a pixel in a set of images includes a value associated with each image at the spatial location corresponding to the pixel.

While each spectral image described above typically refers to a particular combination of excitation and emission wavelengths or range of wavelengths (e.g., a spectral band), more generally, each spectral image can correspond to a spectral index that may include one or more wavelength bands, or some more complex spectral distribution. For example, such an image can be generated by using a spectral comb filter.

Often the image cube includes more than 3 spectral images, for example, 4 or more spectral images (e.g., 5 or more spectral images, 6 or more spectral images, 7 or more spectral images, 8 or more spectral images). However, in some embodiments, the image cube may include fewer images, for example, only two or three spectral images. One such example is an image cube containing two spectral images, one corresponding to emission in the range 450-470 nm, and one corresponding to emission in the range 490-510 nm, in both cases the sample is excited with light in the ultraviolet range 350-380 nm. Optionally, there may be a third image plane corresponding to visible emission while the sample is excited in a visible wavelength band. While such an image cube may be displayed as a single color image, such a color image does not correspond to the visual appearance of the sample; in the examples just given, it corresponds to an image cube that includes two or three spectral images, respectively. Accordingly, the term "image cube" is used to describe cases like this, as well.

Analysis of Multispectral Images

Once the spectral cube of images has been acquired, the image set can be unmixed into separate contributions from each of the counterstains and, if present, IF probes.

As discussed above, in conventional staining protocols, counterstains with well separated spectral absorption and emission profiles are used to identify different regions (e.g., nuclear regions and cytoplasm regions), but this approach can consume much of the visual region of the electromagnetic spectrum, leaving comparatively less spectral room for detecting specific proteins within a sample using IF probes.

In contrast, in the methods and systems disclosed herein, counterstains with similar absorption and emission profiles are used to identify different regions within the sample. However, these stains have very similar color appearance, due to their similar spectral profiles, and have broad spectral overlap.

The particulars of this are evident in FIG. 1, which shows the emission profiles of the two stains. At 460 nm, where CellMarker Blue has its peak emission, DAPI exhibits 60% of its peak emission, and at 500 nm the situation is nearly reversed. At 540 nm, DAPI has fallen to half its peak, but CellMarker Blue is still at approximately 20% of its peak. Thus there is no color, or individual wavelength, at which only the nuclear counterstain emits strongly, without emission from the cytoplasm counterstain, or vice versa. Accordingly one cannot isolate the two signals simply by judicious choice of wavelength.

More generally, as used in this disclosure, two stains have similar absorption profiles if, at the peak absorption wavelength of the first stain, the absorption value of the second stain is at least 30% or more of the peak absorption value of the second stain. Further, two stains have similar emission profiles if, at the peak emission wavelength of the first stain, the emission value of the second stain is at least 30% or more of the peak emission value of the second stain.

Counterstains used in the systems and methods disclosed herein can have absorption and/or emission profiles that overlap to an even larger extent, in some embodiments, as discussed above for CellMarker Blue and DAPI. In general, at the peak absorption wavelength of the first stain, the absorption value of the second stain can be at least 40% or more (e.g., at least 50% or more, at least 60% or more, at least 70% or more, at least 80% or more) of the peak absorption value of the second stain. Similarly, at the peak emission wavelength of the first stain, the emission value of the second stain can be at least 40% or more (e.g., at least 50% or more, at least 60% or more, at least 70% or more, at least 80% or more) of the peak emission value of the second stain.

To separate the spectral contributions of each of these stains in sample images, the image cube can be spectrally unmixed, which produces a set of unmixed images. One of the unmixed images corresponds approximately to contributions from just the nuclear counterstain, and it may be used to identify nuclear regions within the sample. Another of the unmixed images corresponds approximately to contributions from just the cytoplasm counterstain, and it may be used to identify cytoplasm regions within the sample. Other unmixed images correspond approximately to just the contribution from each of the IF probes used, if these are present.

The spectral unmixing procedure essentially consists of decomposing an overall signal at each pixel into a set of spectral eigenstates. Physically, the eigenstates correspond to the spectra of the components in the sample, as presented to the detector. In many embodiments, the spectra are known beforehand, having either been measured from singly-stained control samples, or obtained from reference information. In other embodiments, the spectra may be determined using techniques such as independent component analysis. In either case, once the spectra have been identified, an image cube can be decomposed into its components by calculating a set of values that corresponds to the contribution from each of the spectra to the overall signal at each pixel, and repeating this for all pixels. In this way the image cube is unmixed into its spectral components, to yield the unmixed image set.

As an example, a series of two dimensional images having x and y coordinates can be measured for a sample using several different combinations of excitation wavelengths and emission wavelengths. As described above, the two dimensional images can be combined to form a three-dimensional image cube I(x,y,k) where the first two indices of the image cube represent coordinate directions, and the third index is a spectral index corresponding to the combination of excitation and emission light wavelengths used to acquire that image. Assuming, for the sake of simplicity, that each of the images of the sample contains spectral contributions from two different spectral sources F(k) and G(k), then the values in the three-dimensional image cube I(x,y,k) may be given by $$S(x,y,k)=a(x,y)\cdot F(k)+b(x,y)\cdot G(k) \quad (1)$$

where k is used to denote a given combination of excitation and emission wavelengths (or wavelength bands). The functions a(x,y) and b(x,y) describe the spatial abundance of the spectral contributions from the two different spectral sources in the sample.

According to Equation (1), the net signal any position in the three-dimensional image cube (i.e., at any two-dimensional pixel coordinate, and at a particular combination of excitation and emission wavelengths) is the sum of two contributions, weighted by the relative abundance of each. This can be expressed as $$I(k)=aF(k)+bG(k) \quad (2)$$

The functions F and G can be termed the "spectral eigenstates" for the system because they correspond to the pure spectra for the spectral sources in the sample, which are combined in varying proportions to produce the measured spectral images of the sample. Thus, the sample spectrum is a weighted superposition corresponding to separate contributions from the two spectral sources.

If the spectra F(k) and G(k) are known (or can be deduced), then Equation (2) can be inverted to solve for a and b, provided that spectrum/includes at least two elements (i.e., provided that one has data for at least two spectral configurations k). Equation (2) can be rewritten in matrix form as I=EA, so that $$A=E^{-1}I \quad (3)$$

where A is a column vector with components a and b, and E is a matrix whose columns are the spectral eigenstates, namely [F G].

Using Equation (3), measured spectral images of a sample can be used to calculate contributions to the images arising purely from source F and purely from source G at particular pixel locations. The process can be repeated for each pixel location on a selected image (i.e., throughout the range of values x and y in I) to produce an image of the sample that includes contributions only from source F, and another image of the sample that includes contributions only from source G.

In the above discussion, the number of spectral sources is two (i.e., F and G). In general, however, unmixing techniques are not restricted to any particular number of sources. For example, a sample can generally contain m different spectral sources. If the number of wavelengths at which data is collected is n—that is, k=1 . . . n—then matrix E is an n×m matrix instead of an n×2 matrix, as in the above discussion. The unmixing algorithm can then be employed in the same manner as described above to isolate specific contributions at each pixel location in an image from each of the m spectral eigenstates.

One factor which can limit the ability of the algorithm to distinguish between contributions from different spectral eigenstates is the degree of spectral distinction between the eigenstates. The correlation between two spectra, such as two spectral eigenstates $I_1$ and $I_2$, can be described by a spectral angle θ where $$\theta = \cos^{-1}\left[\frac{I_1 \cdot I_2}{|I_1||I_2|}\right] \quad (4)$$

Sets of spectra for which θ is small for two members are not as easily separated into their components. Physically, the reason for this is easily understood: if two spectra are only marginally different, it is harder to determine the relative abundance of each.

A number of techniques can be used to measure or estimate the pure spectra of the spectral sources F and G (and other spectral sources, where the sample includes more than two). In general, any method that yields spectral eigenstates of sufficient accuracy can be used. One preferred embodiment is to prepare a set of control samples, each of which contains only a single counterstain or IF label, and obtain the eigenstates by measuring the response of each sample in the set for every combination of excitation and emission wavelengths used. Sometimes, a sample is prepared with multiple counterstains, but it is possible to identify a particular pixel or set of pixels in an image of the sample that correspond to only a single type of cellular region, and thus to a particular stain. For example, in an image of a sample counterstained with DAPI and CellMarker Blue, it may be possible to measure the CellMarker Blue spectrum by choosing a point in the image which is adjacent to a nucleus, which contains contributions only, or primarily, from cytoplasm cell regions. The spectrum at one such point, or preferably many such points, may be used to estimate the spectrum of the cytoplasm counterstain.

In some cases, the sample may contains spectral sources such as dyes, quantum dots, or other chemical moieties for which there are known spectra available in published references.

Various data analysis techniques can also be used for determining component spectra for spectral unmixing, such as independent component analysis (ICA), multivariate analysis, and principal component analysis (PCA). In many cases in the life sciences, signal spectra present in the image cube are mixtures of components. If the component of interest is not in a pure form somewhere in the original image cube, then these techniques may not generate an accurate set of spectral estimates for all stains in the sample.

There are some techniques, sometimes called "convex-hull" algorithms, that estimate what the true end-members are even if they do not exist in a pure form in the image, but the effectiveness is dependent on how close signal spectra in the image cube are to the end-members.

One technique that can be used to extract spectral eigenstates (or estimates thereof) without a priori knowledge of all of the eigenstates involves considering the signal spectrum I(k) for a given pixel, and subtracting from it the maximum amount of a first spectral source F(k) while leaving the remaining signal that is positive definite in all spectral channels. That is, one defines a so-called "remainder spectrum" $U_a(k)$ for each pixel as $$U_a(k)=I(k)-aF(k) \quad (5)$$

and then selects the largest value of the parameter a consistent with $U_a(k)$ having a non-negative value in every spectral channel. The resulting spectrum $U_a(k)$ is then used as the signal spectrum, expunged of contributions due to first spectral source F. One may also make the determination of parameter a based not on strict non-negative criterion listed above, but on some related criteria that incorporates a small negative distribution, to account for considerations such as shot noise or detector noise in a measurement system. Additional examples of optimization criteria for removing the maximal amount of spectral source F include using different error functions.

Alternatively, one may seek to extract a contribution to a measured spectrum that is due to second spectral source G. In analogy with Equation (5), the remainder spectrum can be calculated for each pixel as $$U_b(k)=I(k)-bG(k) \quad (6)$$

where one selects the largest value of the parameter b consistent with $U_b(k)$ having a non-negative value in every spectral channel.

The remainder technique can be expanded to cases where the spectra for one or more additional components of the sample are known, and one wants to remove their contributions to the signal. In such cases, the remainder spectrum is written to subtract a contribution of each such component from the observed signal based on the additional spectra and consistent with a positive remainder in each spectral channel.

Additional spectral unmixing techniques are described in PCT Patent Publication No. WO2005/040769 entitled "SPECTRAL IMAGING OF BIOLOGICAL SAMPLES" by Richard Levenson et al., the contents of which are incorporated herein by reference.

In order for the spectral unmixing techniques disclosed herein to effectively separate contributions in sample images that are due to different spectral eigenstates, Equation (1) should be at least approximately correct. That is, the measured spectral data should be approximately described as a linear superposition of weighted eigenstates. This approximation holds for most fluorescence and luminescence measurements made with modern CCD or CMOS detectors, provided the images are properly exposed (i.e. the detector is not saturated), and any gain, brightness or contrast applied to the images is linear with respect to signal level.

Spectral unmixing operations (e.g., matrix inversion techniques and remainder techniques) can be performed by electronic control system 114 via processor 116, for example. These operations can include manual intervention and configuration steps performed by a system operator, or system 100 can be configured to perform these operations in an automated manner.

Image Display and Quantitation

As discussed above, multispectral images (e.g., fluorescence images) of the sample are typically obtained and unmixed into component images, to identify different regions within the sample, and to locate IF probes within different regions of the sample. The information about sample regions and the locations of IF probes can then be used to display a variety of different images to a system operator.

For example, in some embodiments, a digital H&E view is generated. In these views, the sample is rendered as it would appear if it had been stained with H&E and viewed in a brightfield imaging modality. This digital H&E view can be synthesized by acquiring a spectral image cube and unmixing it into a set of component images including images corresponding to the nuclear counterstain and the cytoplasm counterstain, and optionally other stains or IF probes that may be present in the sample; then, rendering an image by starting with a white background, which is multiplied by a blue layer whose opacity at each pixel corresponds to the nuclear counterstain component image value, and further multiplying by a pink layer whose opacity at each pixel corresponds to the cytoplasm counterstain component image value.

Pathologists and others find this kind of view to be very valuable for interpreting the contents of a sample. The systems and methods disclosed herein provide this information in addition to the molecular information provided by the immunofluorescent probes, and the two are complementary.

One way to perform this rendering is using the following equation:

$$RPV=WP \cdot HC^{NNC} \cdot EC^{NCC} \quad (7)$$

where RPV is the rendered {R,G,B} pixel value at a given location, WP is the white point, normally {255,255,255}, HC is the color chosen to represent hematoxylin, such as {0,0,255}, EC is the color chosen to represent eosin, such as {255,0,192}, NNC is the normalized nuclear component value at that pixel, and NCC is the normalized cytoplasm component value at that pixel. In this context, normalized means that the unmixed component images were scaled from their native range (which may be 0-255 for 8-bit images, or 0-4095 for 12-bit images, for example), to a range where 0 corresponds to no stain, and 1 corresponds to moderate or strong stain presence.

The exact blue and pink hue are chosen to match the visual appearance of hematoxylin and of eosin, respectively, and HC and EC may be adjusted to operator preference if that is desired. Similarly, the scaling of the component images can be adjusted to produce a more or less vivid appearance of either component, or both. Brightness, contrast, and gamma corrections can also be applied to the resulting image, if desired. These and other modifications are known to those skilled in the art of computer graphics, and may be undertaken to produce a more pleasing image or a more faithful simulation of an H&E view.

In some embodiments, individual pixels in the image cube are assigned as belonging to either a nuclear region, a cytoplasm region, (or to another type of region), or as no cellular region. This can be done in a variety of ways. In some embodiment, such assignments are performed by comparing pixel values in the unmixed component images against threshold values, and using a rule-set such as: a pixel whose nuclear component signal exceeds a first threshold is declared to be nuclear; otherwise if the pixel's cytoplasm component signal exceeds a second threshold the pixel is declared to be cytoplasm; otherwise, the pixel is not assigned to any cellular region More sophisticated segmentation strategies can also be employed. For example, nuclear regions can be segmented based on the nuclear counterstain unmixed image, using features such as signal strength, texture, smoothing, and so on. Pixels close to a nucleus can be segmented as being cytoplasm regions, provided that their cytoplasm component image signal is within a target range.

The systems and methods disclosed herein provide counterstain-derived information in addition to the molecular information provided by the IF probes; frequently, these two types of information are complementary.

In some embodiments, digital H&E views are provided to a pathologist or other person, enabling the identification of landmarks and regions of interest (or cells of interest) in the sample much more conveniently than by using a conventionally rendered fluorescence image, or by using actual microscope images. Insight about the sample or cells of interest derived from a digital H&E view can enable such a person to choose where to measure the IF signal and/or may alter the interpretation of the signal levels based on the cell structure or morphology. A pathologist or other person can also combine the IF information with an overall visual assessment gained from a digital H&E view to form an overall clinical judgment.

In certain embodiments, images showing the different cellular regions in the sample can be overlaid with one of more of the unmixed images corresponding to the IF probes. In this way, the amount and location of the entities labeled by the IF probes in each of the different cellular regions in the sample can be visualized and quantified. The contributions from each of the IF probes can be color-coded, for example, to aid visual recognition and distinction among the probes. Cells that are highly expressing in one or more of the molecules targeted by the IF probes can be scored as positive, and highlighted or shown with a false-color overlay. The display and quantitation of IF probe signals can be performed for some or all cells within a sample. Information obtained and displayed in this manner is valuable for studies of cell signaling, heterogeneity, and in other situations where one would like to know the statistics for multiple markers within a population of cells.

Hardware and Software

The steps described above in connection with various methods for collecting, processing, analyzing, interpreting, and displaying information from samples can be implemented in computer programs using standard programming techniques, including steps associated with unmixing spectral images to obtain component images corresponding to IF labels and/or counterstains, steps associated with combining/overlaying such images for display, and steps associated with coloring such images to provide visual representations of samples (e.g., providing digital H&E images). Such programs are designed to execute on programmable computers or specifically designed integrated circuits, each comprising an electronic processor (e.g., processor 116), a data storage system (including memory and/or storage elements), at least one input device, and least one output device, such as a display or printer. The program code is applied to input data (e.g., images from the detector) to perform the functions described herein and generate output information (e.g., images showing contributions of sample components, overlays of multiple component images, etc.), which is applied to one or more output devices, such as a user interface that includes a display device. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

EXAMPLES

The subject matter disclosed herein is further described in the following examples, which are not intended to limit the scope of the claims.

Example 1

WM164 cells were prepared according to the following protocol. A slide with eight wells was prepared, and approximately 15,000 cells were placed in each well. The cells were fixed using 167 microliters of 16% formalin solution for 20 minutes. Then they were washed in PBS three times, after which a blocking buffer was applied for 1 hour. After this, the cells were washed in PBS three more times, for five minutes per wash. Following this, CellMask Blue (obtained from InVitrogen, Carlsbad, Calif.) was added in a 1:200 dilution to the antibody diluent, and this was applied for 1 hour. A primary antibody was not included in this experiment. Next, the sample was washed once in PBS with agitation, for 5 minutes. Then, DAPI was applied in a 1:50,000 dilution. Following this, the sample was washed 1× in PBS and then dionized water. Cells were then dried and mounted on the slide.

The slide was viewed in an Olympus BX51 microscope at 40×, using a Semrock LF405/LP-B-000 epi-fluorescence filter. Visually, the nuclear regions and the cytoplasm regions were violet, and could not readily be distinguished from one another. The slide was then imaged using a Vectra® multispectral imaging system (available from PerkinElmer, Waltham, Mass.), using the factory-defined DAPI fluorescence filter band. This produced a multispectral image cube, which was unmixed and analyzed using Nuance® software (also available from PerkinElmer). Unmixed spectra for a nuclear region and a cytoplasm region are shown in FIG. 1.

Figure 2:
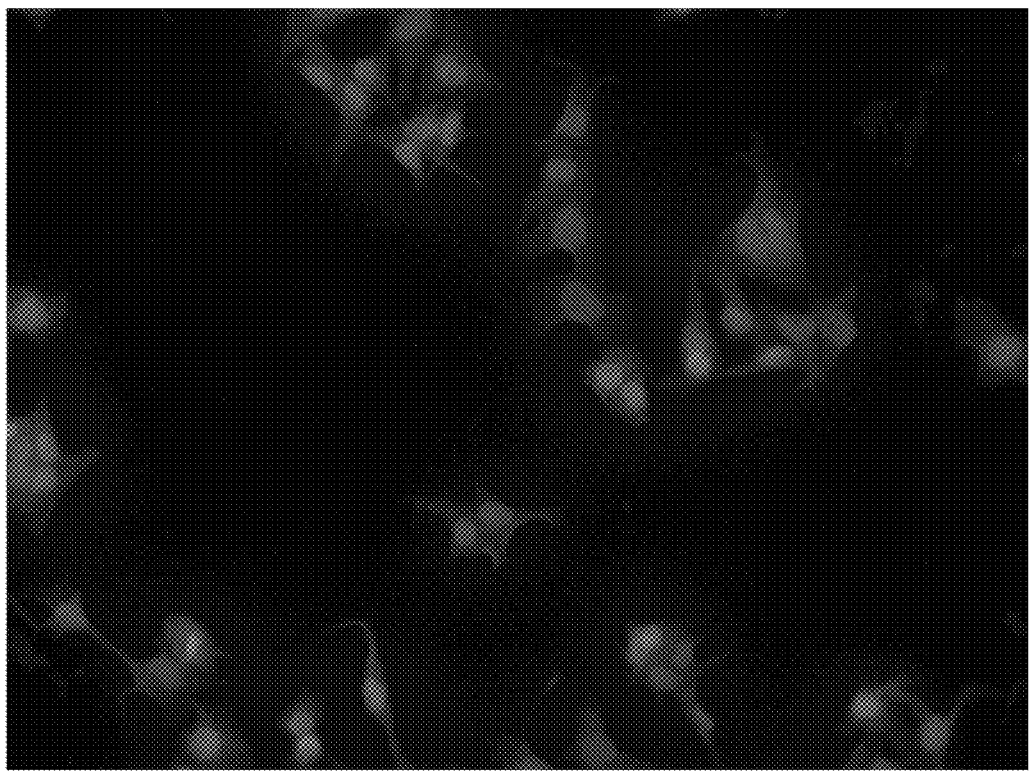
FIG. 2 is an image of a sample prepared with CellMask Blue and DAPI.

The image cube was then analyzed using in Form® (also available from PerkinElmer). The visual appearance of the sample is indicated by the image in FIG. 2. This image is the visual rendering of the multispectral image cube, produced by in Form® using its human eye rendering algorithm. As shown in FIG. 2, the nuclear and cytoplasm regions were not clearly distinguishable.

Figure 3:
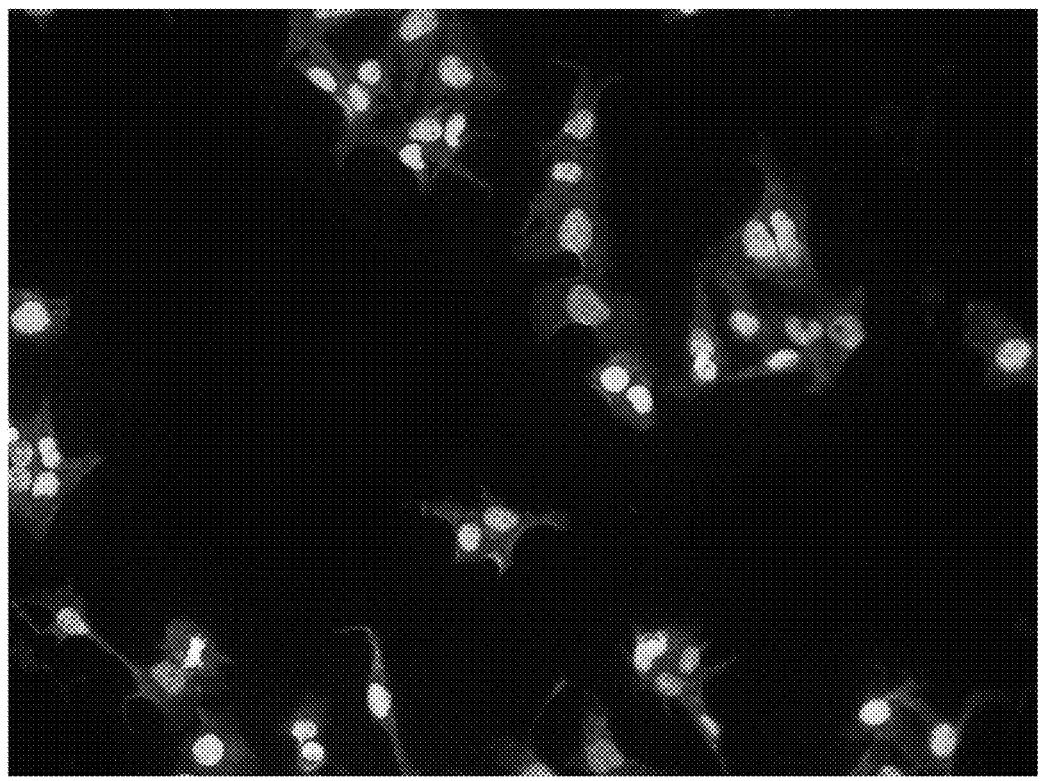
FIG. 3 is an image of the sample of FIG. 2 showing nuclear and cytoplasm components; the dark grey regions correspond to cytoplasm, and the light grey regions correspond to the nuclear component.

The image cube was then unmixed using the spectra shown in FIG. 1, and a fluorescence composite image was generated using the in Form® composite tool, shown in FIG. 3. The CellMask Blue component signal was rendered in red (dark grey in FIG. 3), and the DAPI component signal was rendered in cyan (light grey in FIG. 3). Where both were present, the pixels were rendered in white.

Figure 4:
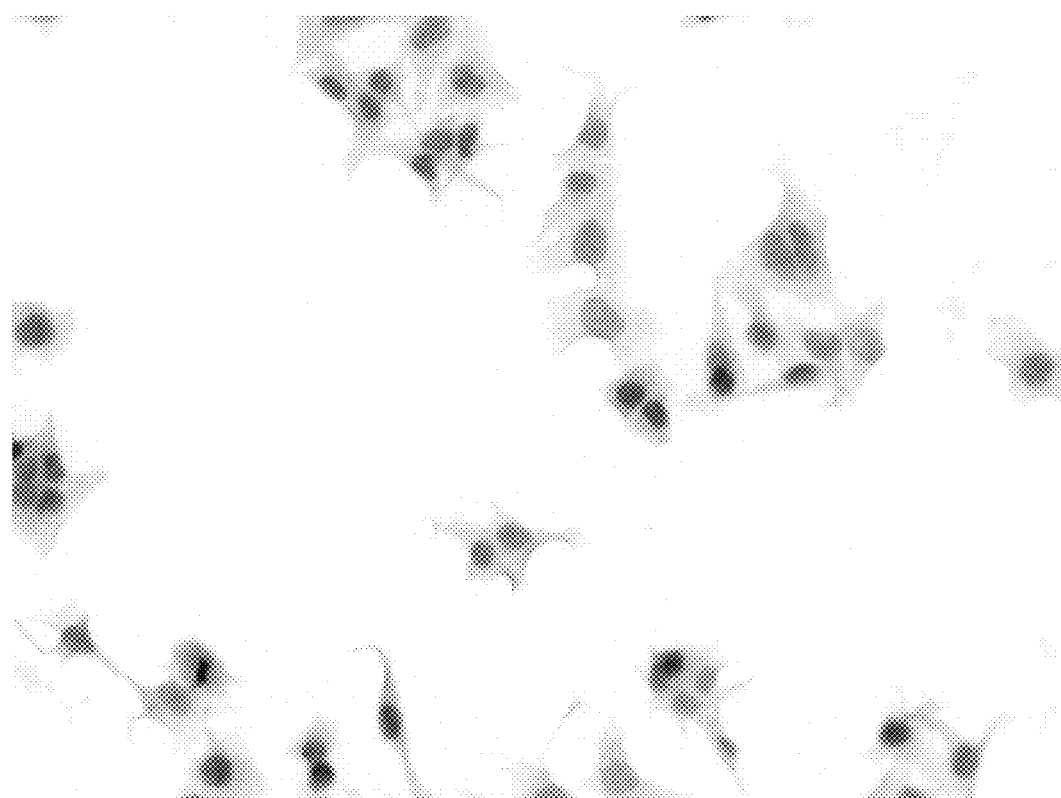
FIG. 4 is an image of the sample of FIG. 2 shaded to show how the sample would appear if it was stained with H&E.

Another image was generated using in Form®, using a brightfield rendering style. In this case, the CellMask Blue component was rendered using a pink color, and the overall result has the appearance of an H&E preparation. A greyscale version of the rendered image is shown in FIG. 4.

Figure 5:
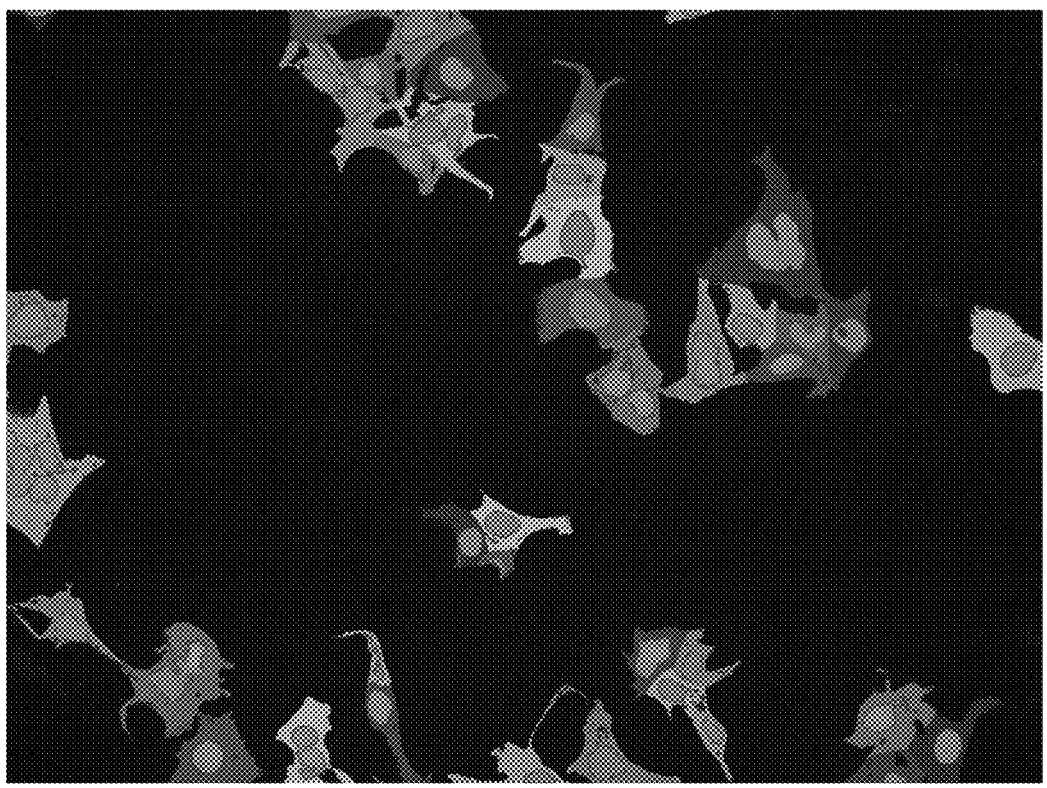
FIG. 5 is an image of the sample of FIG. 2 in which cytoplasm and nuclear components of each cell are segmented and rendered as overlays on the image.

The image was then segmented using in Form®, using a nuclear segmentation based on the DAPI signal to locate the nuclei. The cytoplasm segmentation included a signal-validation range based on the CellMask Blue, so that only pixels whose component strength was above a minimum threshold were included in the cytoplasm compartment. The segmented image is shown in FIG. 5.

Example 2

Primary antibodies for ki67, pERK, pAKT, S6, and S100 were applied to the sample and conjugated with AlexaFluor 488, AlexaFluor 532, AlexaFluor 555, AlexaFluor 594, AlexaFluor 647. They were imaged with the Vectra® using its DAPI, FITC, Cy3, Wide Green, and Cy5 filter bands.

Other Embodiments

A number of embodiments have been described. Nevertheless, it will be understood that various modifications may be made without departing from the spirit and scope of the disclosure.

For example, while DAPI was used in the examples to identify nuclear regions within samples, other stains such as Hoechst 33258 can also be used for this purpose.

In addition, a variety of different IF probes (e.g., primary antibodies) can be used to label proteins within the sample. For example, two or more IF probes (e.g., three or more, four or more, five or more, six or more, seven or more, eight or more) IF probes can be applied to a sample.

The entire disclosures of each of the following U.S. patent applications are incorporated herein by reference: Ser. No. 12/251,632, filed on Oct. 15, 2008; Ser. No. 12/564,857, filed on Sep. 22, 2009; and Ser. No. 13/204,173, filed on Aug. 5, 2011.

Other embodiments are in the claims.

What is claimed is:

1. A system, comprising:
a detector configured to obtain multiple images of a sample stained with first and second counterstains, wherein the first and second counterstains have similar spectral absorption and emission profiles; and
an electronic processor configured to:
decompose the multiple images into an unmixed image set, wherein the unmixed image set comprises a first unmixed image corresponding to the first counterstain and a second unmixed image corresponding to the second counterstain; and
identify nuclear regions in the sample based on the first unmixed image and identify cytoplasm regions in the sample based on the second unmixed image.

2. The system of claim 1, wherein the electronic processor is further configured to generate an image of the sample, and wherein the nuclear and cytoplasm regions in the image are colored in the same manner as if the sample was stained with hematoxylin and eosin.

3. The system of claim 1, wherein the sample comprises one or more immunofluorescent probes, and wherein the unmixed image set comprises unmixed images that each correspond to contributions from only one of the immunofluorescent probes.

4. The system of claim 3, wherein the electronic processor is further configured to determine an amount of at least some of the immunofluorescent probes in the nuclear and cytoplasm regions in the sample.

5. The system of claim 3, wherein the sample comprises at least three immunofluorescent probes.

6. The system of claim 3, wherein the sample comprises at least five immunofluorescent probes.

7. The system of claim 1, wherein the multiple images comprise fluorescence images.

8. The system of claim 1, wherein the second stain is CellMask Blue.

9. The system of claim 8, wherein the first stain is DAPI.

10. The system of claim 8, wherein the first stain is Hoechst 33258.

11. The system of claim 1, wherein the multiple images define an image cube.

12. The system of claim 1, wherein each of the multiple images corresponds to a fluorescence image of the sample for a different corresponding range of fluorescence wavelengths.

13. The system of claim 1, further comprising a multi-spectral imaging system coupled to the detector, wherein the multi-spectral imaging system is configured to illuminate the sample to obtain the multiple images.

14. A method, comprising:
applying at least two counterstains to a sample, wherein the at least two counterstains have similar spectral absorption and emission profiles; and
using an electronic processor to:
obtain multiple images of the sample;
obtain a first unmixed image corresponding to a first one of the counterstains and a second unmixed image corresponding to a second one of the counterstains; and
identify nuclear regions in the sample based on the first unmixed image and identify cytoplasm regions in the sample based on the second unmixed image.

15. The method of claim 14, further comprising using the electronic processor to:
decompose the multiple images into an unmixed image set, wherein the unmixed image set comprises the first unmixed image and the second unmixed image.

16. The method of claim 15, further comprising using the electronic processor to generate an image of the sample, wherein the nuclear and cytoplasm regions in the image are colored in the same manner as if the sample was stained with hematoxylin and eosin.

17. The method of claim 15, wherein the sample comprises one or more immunofluorescent probes, and wherein the unmixed image set comprises unmixed images that each correspond to contributions from only one of the immunofluorescent probes.

18. The method of claim 17, further comprising using the electronic processor to determine an amount of at least some of the immunofluorescent probes in the nuclear and cytoplasm regions in the sample.

19. The method of claim 17, wherein the sample comprises at least three immunofluorescent probes.

20. The method of claim 17, wherein the sample comprises at least five immunofluorescent probes.

21. The method of claim 15, wherein the multiple images comprise fluorescence images.

22. The method of claim 14, wherein the at least two stains comprise CellMask Blue and DAPI.

23. The method of claim 14, wherein the at least two stains comprise CellMask Blue and Hoechst 33258.

24. The method of claim 14, wherein the multiple images define an image cube.

25. The method of claim 14, wherein each of the multiple images corresponds to a fluorescence image of the sample for a different corresponding range of fluorescence wavelengths.

26. A system, comprising:
a detector configured to obtain multiple images of a sample stained with first and second stains, wherein the first stain comprises DAPI or Hoeschst 33258 and the second stain comprises CellMask Blue; and
an electronic processor configured to:
decompose the multiple images into an unmixed image set, wherein the unmixed image set comprises a first unmixed image corresponding to the first stain and a second unmixed image corresponding to the second stain; and
identify nuclear regions in the sample based on the first unmixed image and identify cytoplasm regions in the sample based on the second unmixed image.

27. The system of claim 26, wherein the electronic processor is further configured to generate an image of the sample, and wherein the nuclear and cytoplasm regions in the image are colored in the same manner as if the sample was stained with hematoxylin and eosin.

28. The system of claim 26, wherein the sample comprises one or more immunofluorescent probes, and wherein the unmixed image set comprises unmixed images that each correspond to contributions from only one of the immunofluorescent probes.

29. The system of claim 28, wherein the electronic processor is further configured to determine an amount of at least some of the immunofluorescent probes in the nuclear and cytoplasm regions in the sample.

30. A method, comprising:
applying at least two stains to a sample, wherein the first stain comprises DAPI or Hoeschst 33258 and the second stain comprises CellMask Blue; and
using an electronic processor to:
obtain multiple images of the sample;
obtain a first unmixed image corresponding to the first stain and a second unmixed image corresponding to the second stain; and
identify nuclear regions in the sample based on the first unmixed image and identify cytoplasm regions in the sample based on the second unmixed image.

31. The method of claim 30, further comprising using an electronic processor to:
decompose the multiple images into an unmixed image set, wherein the unmixed image set comprises the first unmixed image and the second unmixed image.

32. The method of claim 31, further comprising using the electronic processor to generate an image of the sample, wherein the nuclear and cytoplasm regions in the image are colored in the same manner as if the sample was stained with hematoxylin and eosin.

33. The method of claim 31, wherein the sample comprises one or more immunofluorescent probes, and wherein the unmixed image set comprises unmixed images that each correspond to contributions from only one of the immunofluorescent probes.

34. The method of claim 33, further comprising using the electronic processor to determine an amount of at least some of the immunofluorescent probes in the nuclear and cytoplasm regions in the sample.

* * * * *

UNITED STATES PATENT AND TRADEMARK OFFICE
CERTIFICATE OF CORRECTION

PATENT NO. : 10,032,064 B2
APPLICATION NO. : 13/972119
DATED : July 24, 2018
INVENTOR(S) : Clifford C. Hoyt Page 1 of 1

It is certified that error appears in the above-identified patent and that said Letters Patent is hereby corrected as shown below:

In the Claims

Column 19
Line 27, in Claim 26, delete "Hoeschst" and insert -- Hoechst --

Column 20
Line 12 (Approx.), in Claim 30, delete "Hoeschst" and insert -- Hoechst --

Signed and Sealed this
Second Day of October, 2018

Andrei Iancu
*Director of the United States Patent and Trademark Office*